(12) United States Patent
Franklin et al.

(10) Patent No.: US 8,041,751 B2
(45) Date of Patent: *Oct. 18, 2011

(54) SYSTEMS AND METHODS FOR DECODING PAYER IDENTIFICATION IN HEALTH CARE DATA RECORDS

(75) Inventors: Dave Franklin, Lansdale, PA (US); Ilene Blanton, Washington Crossing, PA (US); Mary Kay James, Broheadsville, PA (US); Kevin Moyer, Hatfield, PA (US); Kimberly Pennente, Maple Glen, PA (US)

(73) Assignee: IMS Software Services, Ltd., Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/782,423

(22) Filed: May 18, 2010

(65) Prior Publication Data

US 2010/0228569 A1    Sep. 9, 2010

Related U.S. Application Data

(63) Continuation of application No. 10/893,838, filed on Jul. 19, 2004, now Pat. No. 7,747,658.

(60) Provisional application No. 60/488,692, filed on Jul. 18, 2003.

(51) Int. Cl.
*G06F 7/00* (2006.01)
*G06F 17/00* (2006.01)
*G06Q 10/00* (2006.01)
*G06Q 50/00* (2006.01)

(52) U.S. Cl. .............. 707/809; 707/941; 705/5

(58) Field of Classification Search .......... 707/809, 707/941

See application file for complete search history.

*Primary Examiner* — John R. Cottingham
*Assistant Examiner* — Mariela Reyes
(74) *Attorney, Agent, or Firm* — Baker Botts L.L.P.

(57) ABSTRACT

Processing arrangements and methods are provided for the automated decoding or translation of information in healthcare data records, which are coded in a non-standardized or varying formats. A data record which contains information, a portion which is recognized and another portion of which is new, is decoded or translated using a statistical mapping rule. The mapping rule assigns a most likely translation value to the information based on the recognized portion of the information. The statistical mapping rules are established by analysis of a set of previously decoded data records.

5 Claims, 3 Drawing Sheets

FIG. 2

| BIN | Group ID | PCN | Plan Code | | OTHER INDICIA |
|---|---|---|---|---|---|
| 610014 | OXFRDHP | 7Q 7790529 | 333 | - - - | X Y Z Z |

SYSTEMS AND METHODS FOR DECODING PAYER IDENTIFICATION IN HEALTH CARE DATA RECORDS

CROSS-REFERENCE TO RELATED APPLICATIONS

This application is a continuation of U.S. patent application Ser. No. 10/893,838, filed Jul. 19, 2004, now U.S. Pat. No. 7,747,658 which claims the benefit of U.S. provisional patent application Ser. No. 60/488,692, filed Jul. 18, 2003.

BACKGROUND OF THE INVENTION

The present invention relates to techniques for analysis of health care and pharmaceutical data. The invention in particular relates to the correlation of specific managed health care payers and plans with prescription data records that contain non-standardized health care payer and plan identifiers.

Prescription data records that are generated by retail pharmacies or hospital dispensaries, for example, when they fill prescriptions for customers, contain labels or data fields that include information identifying the party responsible for authorizing and/or making payments for the prescriptions. Useful market intelligence may be derived from statistical or other analysis of the responsible party information and other information in the prescription data records. The useful market intelligence may, for example, include competitive assessments of the marketing and sales of a particular product, which may be of interest to a pharmaceutical concern, or health care provider or agency.

The prescription data records may include information, which relates to the party responsible for authorizing and/or making payments, in one more data fields such as Bank Identification Numbers ("BINs"), Processor Control Numbers ("PCNs"), and health care plan Group Identification Numbers ("Group IDs"). The BIN data field may for example, contain a six-digit number that codes information about the adjudicator of the prescription drug claim or script.

Unfortunately, the type and number of such data fields may vary with each generator or source of the prescription data records. The prescription data records formats also may change in time. Further, the information in the data records is often coded in a non-standardized format. The labels and other coded information in the prescription data records must be decoded before full analysis of the data records can take place. In practice, a market research organization or other party analyzing the prescription data records may undertake to build a glossary or dictionary of the labels or codes that are found in data fields such BIN, PCN or Group ID.

The market research organization may manually verify the codes entered in the glossary or dictionary. On encountering a new label or code in a prescription data record, the market research organization may, for example, make manual inquires (e.g., via telephone calls) to individual retail pharmacy organizations or pharmacy benefit management companies ("PBMs") in order to verify the meaning of the code. Such manual verification procedures can be both laborious and expensive. Furthermore, the manual verification procedures may not be always successful or complete. The success of the manual verification procedures depends on the responsiveness of the third parties, who may not be obligated to respond.

Consideration is now being given to ways of enhancing procedures for decoding information contained in prescription data records. Attention is directed to procedures for verifying the meaning of codes and labels in prescription data records that relate, for example, to the identity of parties responsible for authorizing and/or making payments. The desirable procedures may be automated, thereby minimizing the need to contact other parties for code verification.

SUMMARY OF THE INVENTION

In accordance with the present invention, data processing arrangements and automated procedures are provided for translating the varying codes and labels that are used in prescription data records to identify or mark involved parties.

The inventive data processing arrangement develops translation or mapping rules based on a set of previously mapped data records. A previously mapped data record in the set may have been assigned a translation value or "ID" based on the content or values of a plurality of data fields (e.g., three data fields) in the data record. The data processing arrangement is configured to first identify unique combinations of the values of a lesser number of the data fields (e.g., two data fields) occurring in the set of previously mapped data records. Then for each unique combination of the values of the lesser number of data fields, the data processing arrangement determines the statistical frequency of ID assignments in the set of previously mapped data records. Mapping rules, which assign a frequently occurring ID to other data records based on the content of the lesser number of data fields (e.g., two data fields), are then established. Thus, even when the values of a data field (e.g., the third data field) in a data record are not recognized or are new, the mapping rules allow assignment of an ID to the data record based on recognized combinations of the values of the lesser number of data fields. The mapping rules may be validated or verified by data suppliers, and assembled for use in a look-up table In a preferred embodiment of the invention, the frequently occurring ID assigned by the mapping rules is the most frequently occurring or most likely ID found in the previously mapped set of data records.

Further features of the invention, its nature, and various advantages will be more apparent from the following detailed description and the accompanying drawings,

BRIEF DESCRIPTION OF THE DRAWINGS

FIG. 2 is a schematic representation of the format of a prescription transaction data record.

Throughout the figures, unless otherwise stated, the same reference numerals and characters are used to denote like features, elements, components, or portions of the illustrated embodiments.

DETAILED DESCRIPTION OF THE INVENTION

The present invention provides solutions for translating or decoding information in health care data records, which is coded in a non-standardized or varying formats. The solutions may be implemented in conventional computer data processing arrangements so that electronic health care data records can be processed automatically. The solutions utilize continuous learning algorithms to decode new information, which at least partially overlaps with the previously mapped or decoded information. The learning algorithms exploit previously validated mappings of information as bridges to decode and establish mapping rules for the partially overlapping new information. The mapping rules for the new information may be validated or verified on a statistical basis. The validated mapping rules are assembled in a bridge table or reference file for convenience in use.

For purposes of describing applications of the invention, prescription transaction data records are used as the exemplary health care data records, herein. FIG. 2 shows the format of an exemplary prescription transaction record 200, which may be prepared by a retail pharmacy in the course of filling a prescription request by a customer. The prescription transaction data record may be part of an electronic data file that is assembled by a data supplier/vendor, and made available for analysis (e.g., to market researchers). Prescription transaction data record 200 may include one or more data fields (e.g., BIN, PCN or Group ID) that include coded information on the parties (e.g., banks, processors, health insurance plans) that are involved in authorizing or making payments for the prescription.

Data record 200 also may include an alternate or additional fourth field ("DS"), which includes data supplier specified codes for the payer ("DS payer codes"). The DS payer codes in a data record might be payer identification codes that are assigned to payers by independent choice or practice of the data supplier or data record preparer. Different suppliers and data record preparers may choose varying formats for the DS payer codes. Other data fields in data record 200 also may include other supplier/preparer specified indicia in varying formats.

Figure 1A:
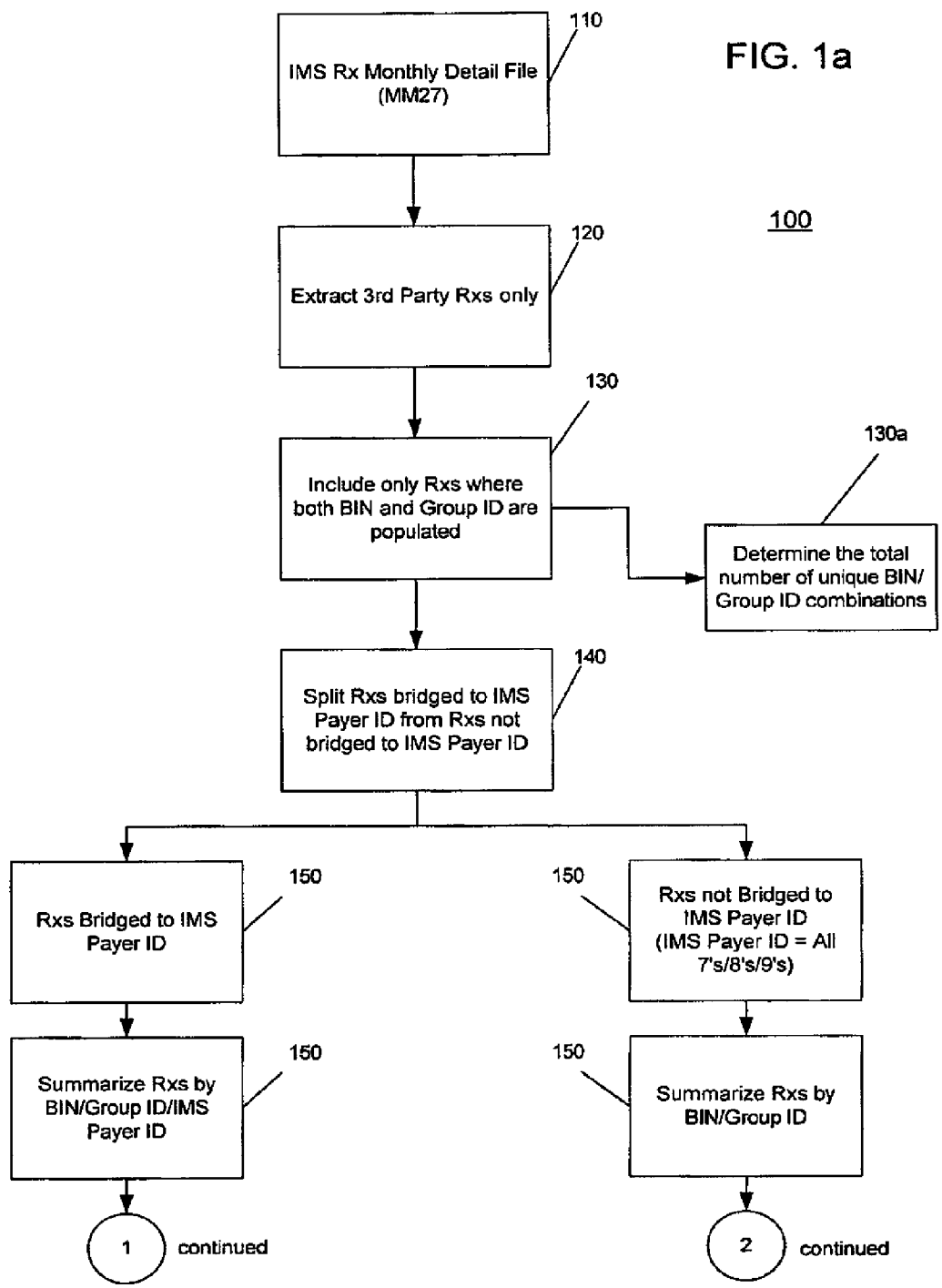
FIGS. 1a and 1b are flow diagrams, which illustrate several of the steps in an exemplary procedure for verifying payer identification codes in prescription data records, in accordance with the principles of the present invention.
Figure 1B:
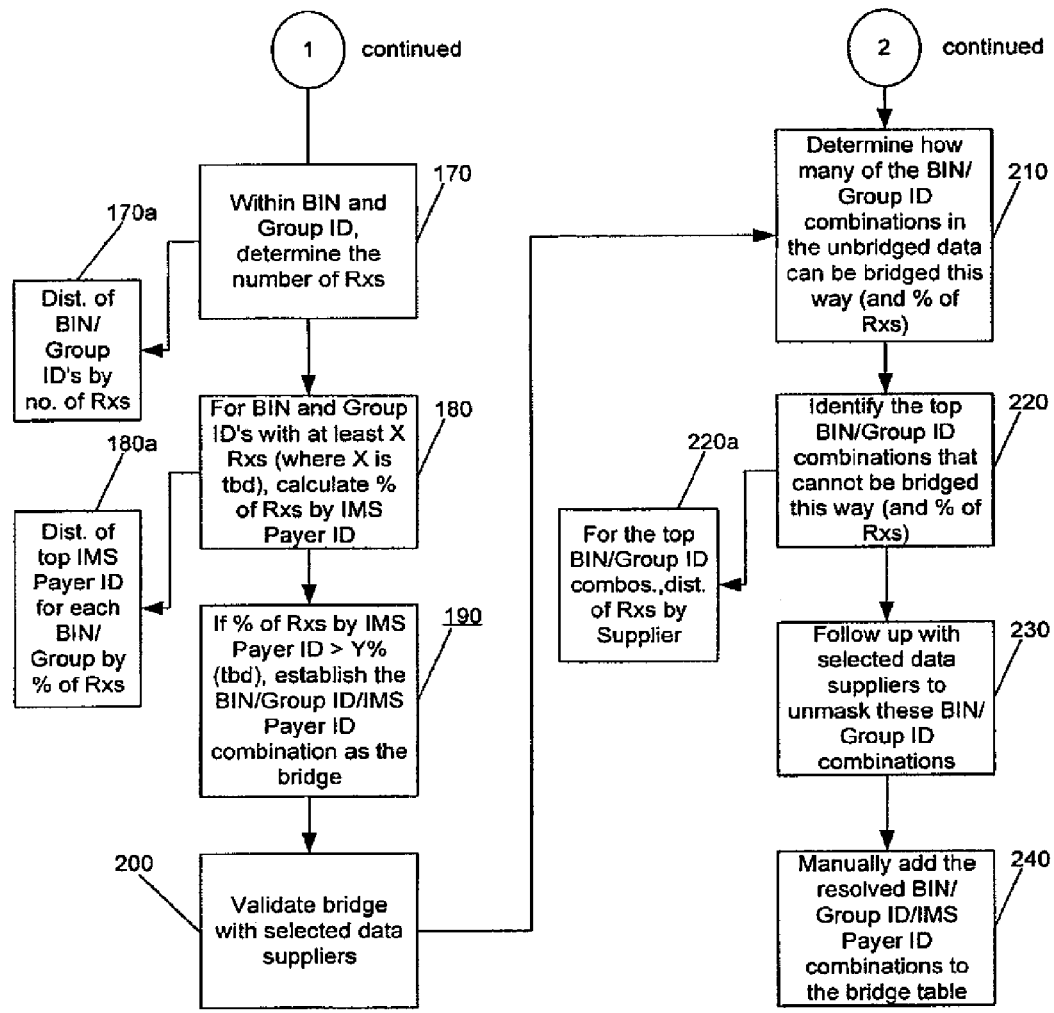

FIGS. 1a and 1b show the steps of an exemplary learning procedure 100 for mapping non-standardized information in health care records. Procedure 100 may be used so that the non-standardized information may be used to categorically identify or associate specific third parties (e.g., specific managed health care payers and plans) with the specific health care records. Procedure 100 may be advantageously used by a market researcher or analyst ("MR"), for example, to relate specific managed health care payers and plans ("payer") to specific prescription transaction data records. As a preliminary step, the MR may establish a comprehensive identification list of payers. Each payer in the list may be uniquely associated with a unique MR code ("MR payer code"). The MR payer code may, for example, be a six-character alphanumeral.

At step 110, MR acquires a file of prescription transactions data records ("Rx file") for analysis. The prescription transaction records in the Rx file may, for example, include information on retail prescription transactions conducted in any suitable market region or segment of interest. Further, the prescription transactions data records in the Rx file may span any suitable time interval of interest (e.g., a week, month or quarter).

The data records in the Rx file may be acquired directly from retailers (e.g., independent pharmacies or drug store chains) by the MR itself or acquired using the services of intermediary commercial data vendors or suppliers. The prescription transaction data records may include one or more data fields (e.g., BIN, PCN, Group ID, DS) that include coded information on the prescription payers. (See e.g., FIG. 2). The DS data field may include data supplier/preparer specified codes for the payer ("DS payer codes") in varying formats. Additional data fields may include other supplier specified indicia. The data supplier may in some instances make available to the MR a glossary of the DS payer codes. The glossary may, for example, indicate that a code "xxyy" refers to "XYZ" health insurance company.

The data records in the Rx file or similar data records may previously have been processed using procedures other than procedure 100 (e.g., manual verification procedures or data supplier glossaries) to decode the identity of parties responsible for authorizing and/or making payments for at least some of the data records.

At step 120 of procedure 100, the prescription transaction data records in the Rx file are processed to retain only those transactions that involve a third party payer (i.e., a health care plan). At this step, all cash transactions, which, for example, are fully paid for by the retail customers, are excluded from the Rx file under analysis. Prescription transactions that are covered by Medicaid or other government initiatives also may be excluded from the Rx file. Thus, only "non-cash" transactions that include information about a third party payer are retained in the Rx file. The percentage of non-cash transactions in a typical Rx file under present pharmaceutical market conditions may be about 75%.

Next at step 130, a "populated" set of prescription transaction records in which both of the BIN and Group ID data fields are populated is identified. Optionally in some implementations of process 100, data transaction records, which alternately or additionally have the PCN data fields populated also may be included in the "populated" set of data transaction records. Similarly, the populated set of data transaction records may further include data transactions in which the DS field is populated with data supplier specified payer codes. At associated step 130a, the populated set of data records may be analyzed to identify the number of and to update a list of all unique combinations of BIN and Group ID values found in the data records. In implementations where PCN data fields are also considered, the identification of unique combinations of BIN and Group ID values may be extended to include PCN values as appropriate.

At step 140 of procedure 100, the populated set of prescription transaction records is separated into two subsets A and B. The first subset A includes prescription transaction records whose BIN and Group ID combinations have been previously mapped to corresponding payers (i.e. MR payer codes). These prescription transaction records may have been previously mapped using, for example, recognizable DS codes and supplier glossaries. Conversely, the second subset B includes prescription transaction data records whose DS codes or other supplier indicia have not been previously mapped to or associated with specific payers. In other words the DS codes or other supplier indicia values are new or not recognized.

At optional step 150, the data records in subset A may be encoded with the mapped MR payer ID corresponding to the combinations of BIN and Group ID values in the records. Similarly, the data records in subset B may be encoded with the dummy MR payer ID values (e.g., all 7s, 8s or 9s) to indicate that the DS codes or other supplier indicia in the records are new and have not yet been mapped to MR payer ID values.

In learning procedure 100, the subset A data records and associated mapping information are advantageously used to learn mapping rules that can be applied to the new data field combinations (e.g., those found in subset B data records).

The distribution of the number of data records in each subset A and B by data field value may then be computed. First, for example, at step 160 the mapped prescription data records in subset A may be sorted by, or binned or grouped for each unique combination of data field values (e.g., combinations of BIN and Group ID values, or combinations of BIN, Group ID and PCN values) present in subset A. Similarly, the unmapped prescription transaction data records in subset B may be sorted, binned or grouped for each unique combination of BIN and Group ID values present in subset B.

As part of the learning process, statistical analysis (e.g., frequency distribution analysis of data field values in subset A) is conducted. At step 170, the number of prescription transaction data records for each unique combination of data field values is counted. This step yields, for example, a frequency distribution of the unique BIN and Group ID combinations across the prescription data records in subset A (step 170a).

Using the frequency distribution results of step 170, data field value combinations that have only a few associated prescription transaction data records may be dropped from further consideration in the learning process. For example, data field value combinations that have frequency counts that are less than a suitable cutoff number X, may be dropped from further consideration. The suitable cutoff number X may be selected on the basis of statistical theories of sample size, or empirically by trial and error use of procedure 100. Only data record groups corresponding to data field combinations that have an occurrence frequency greater than the cutoff limit X may be considered to have sample sizes of sufficient statistical significance.

At step 180 and 180a, these remaining data field combinations in subset A are analyzed to determine the frequency distribution of associated prescription data records by MR payer ID to which they (data records) are mapped. For each unique data field value combination (e.g., BIN and Group ID combination) and each mapped MR payer ID, the percentage of prescription data records mapped to the MR payer ID is computed.

As in the case of the distribution of data field combinations (steps 170 and 170a), MR payer IDs that have only a few associated prescription transaction data records may be dropped from further consideration in the learning process. For example, at step 190 prescription data records that are associated with MR payer IDs that occur with a frequency of less than cutoff limit Y % may be dropped from consideration. Like the cutoff number X, the cutoff limit Y % may be selected on the basis of statistical theories on sample size or empirically by trial and error.

Further at step 190, each combination of unique data field values (e.g., BIN, Group ID and/or PCN) and its mapped MR payer ID, which has an occurrence frequency greater than Y %, is established as a "mapping bridge" These mapping bridges represent the mapping information learnt from subset A. Such learnt mapping bridges may be applied to data records with unrecognized DS codes and other supplier indicia to map or associate these data records to MR payer IDs. The learnt mapping bridges may, for example, be assembled or listed in a bridge table so that they can utilized in the manner of a lookup table in automated data processing arrangements. The mapping bridges may first be validated at optional step 200, for example, by manually verifying the correlation of the specific combinations of BIN, Group ID and/or PCN and specific MR payer IDs with selected data suppliers.

Steps 210-240 shown in FIG. 1b, are exemplary steps that show the application of the learnt mapping bridges to address the problem of mapping the prescription transaction data records in subset B (or other data files) that have unrecognized DS or other supplier indicia. At step 210, a determination is made of which BIN and Group ID value combinations in subset B have corresponding MR payer ID entries in the mapping bridge table. All the prescription transaction data records associated or binned with a specific BIN/Group ID (e.g., step 160) may then be assigned the corresponding MR payer ID entry shown in the mapping bridge table.

At step 220 and 220a, the remaining BIN and Group ID value combinations, which do not have entries in the mapping bridge table, may be further to extract additional information. The number of prescription transaction data records associated with each of the remaining BIN and Group ID value combinations may be counted. For the each of remaining combinations associated with a large number of prescription transaction data records, the distribution of data records by data supplier may be computed. At step 230, selected data suppliers may, for example, be requested to assist in decoding or resolving DS codes and other supplier indicia so that these can be correlated to the MR payer IDs. At step 240, newly resolved BIN/Group ID and MR payer ID combinations may be added to the mapping bridge table for future use.

It will be understood that the particular sequence of steps in learning procedure 100 described above is exemplary. The steps may be performed in any suitable sequence and particular steps may be omitted or modified. Alternate or additional steps may be added to procedure 100 as suitable or appropriate, for example, for modifications of procedure 100 which employ alternative statistical or matching models. Further, the steps of procedure 100 may be implemented in data processing arrangements using any suitable combination of computer hardware elements and software applications.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

The invention claimed is:

1. A method for establishing mapping rules for assigning codes to prescription transaction data records, wherein each data record comprises at least a first, a second and a third data field, the method comprising:
   receiving a set of previously mapped data records in which codes have been assigned to the data records based on at least the values of the third data fields;
   determining a unique combination of first and second data field values present in the set of previously mapped data records;
   determining a code that is assigned to the data records having the unique combination of first and second data field values with an acceptable frequency; and
   storing a mapping rule that maps the code to the unique combination of first and second data field values,
   wherein the mapping rule is stored only for the unique combinations of the first and second data field values that occur with a frequency greater than a cutoff limit.

2. The method of claim 1, wherein each data record comprises at least a first, a second, third, and fourth data field, the method further comprising:
   determining a unique combination of first, second and fourth data field values present in the set of previously mapped data records;
   determining a code that is assigned to the data records having the unique combination of first, second, and fourth data field values with an acceptable frequency; and
   storing a mapping rule that maps the code to the unique combination of first, second, and fourth data field values,
   wherein the mapping rule is stored only for the unique combinations of the first, second, and fourth data field values that occur with a frequency greater than a cutoff limit.

3. A method for assigning codes to prescription transaction data records, comprising:
- receiving a first and a second subset of data records of the prescription transaction data records, wherein the prescription transaction records include at least a first, second, and third data field, wherein data records in the first subset have been previously assigned codes based on known mappings of the values in their respective third data fields, and wherein data records in the second subset have not been previously assigned codes;
- for each data record in the first subset, identifying data records in which at least one of the first and second data fields are populated with data values;
- determining unique combinations of data values of the first and second data fields present in the first subset;
- determining the occurrence frequency of each unique combination of the data values of the first and second data fields in the first subset;
- identifying the unique combinations of first and second data values that occur with a frequency greater than a cutoff limit X;
- for each of the identified unique combination of first and second data values, determining the frequency distribution of codes assigned to data records in the first subset having the corresponding unique combination;
- identifying codes in the frequency distribution for each unique combination having an occurrence frequency greater than a cutoff limit Y; and
- for each identified code, storing the combination of the first and second data values and the identified code as a mapping rule for mapping data records in the second subset of data records.

4. The method of claim 3, further comprising:
assigning codes to data records in the second subset based at least in part on matching the first and second data values of the data records in the second subset with one of the unique combinations of data values and applying a corresponding mapping rule.

5. The method of claim 3, wherein the first subset includes historical data records.

* * * * *